United States Patent
Brown

[19]

[11] Patent Number: 6,131,573
[45] Date of Patent: Oct. 17, 2000

[54] APPARATUS AND METHOD OF MANUFACTURING PULMONARY FUNCTION FILTER

[75] Inventor: Daniel G. Brown, San Clemente, Calif.

[73] Assignee: Vickie Natale-Brown, San Clemente, Calif.

[21] Appl. No.: 08/823,239

[22] Filed: Mar. 24, 1997

[51] Int. Cl.[7] .................................................. A61M 16/00
[52] U.S. Cl. .......................... 128/205.27; 128/202.28; 128/205.29; 210/445
[58] Field of Search .................... 128/205.27, 202.28, 128/201.13, 205.12, 204.17, 205.29, 203.11; 55/500, 491, 497, 540, 511; 210/445, 446

[56] References Cited

U.S. PATENT DOCUMENTS

| | | | |
|---|---|---|---|
| 294,244 | 2/1884 | Lewis et al. | 210/445 |
| 604,931 | 5/1898 | Eisendrath | 210/445 |
| 973,723 | 10/1910 | Thomson | 210/445 |
| 3,782,083 | 1/1974 | Rosenberg | 128/205.12 |
| 3,932,153 | 1/1976 | Byrns | 55/511 |
| 4,148,732 | 4/1979 | Burrow et al. | 210/445 |
| 5,195,527 | 3/1993 | Hicks | 128/205.27 |
| 5,885,455 | 3/1999 | Graus et al. | 210/445 |

FOREIGN PATENT DOCUMENTS 2244790  12/1991  United Kingdom .............. 128/205.12

*Primary Examiner*—John Weiss
*Assistant Examiner*—V. Srivastava
*Attorney, Agent, or Firm*—Henricks, Slavin & Holmes LLP

[57] ABSTRACT

A pulmonary function filter is disclosed having a housing with an inlet and an outlet and a perimeter edge formed by an upper perimeter element and a lower perimeter element. The filter includes a perimeter element having a perimeter edge positioned between the upper and lower perimeter elements and wherein the filter element perimeter edge follows a path extending at least partially back on itself.

10 Claims, 3 Drawing Sheets

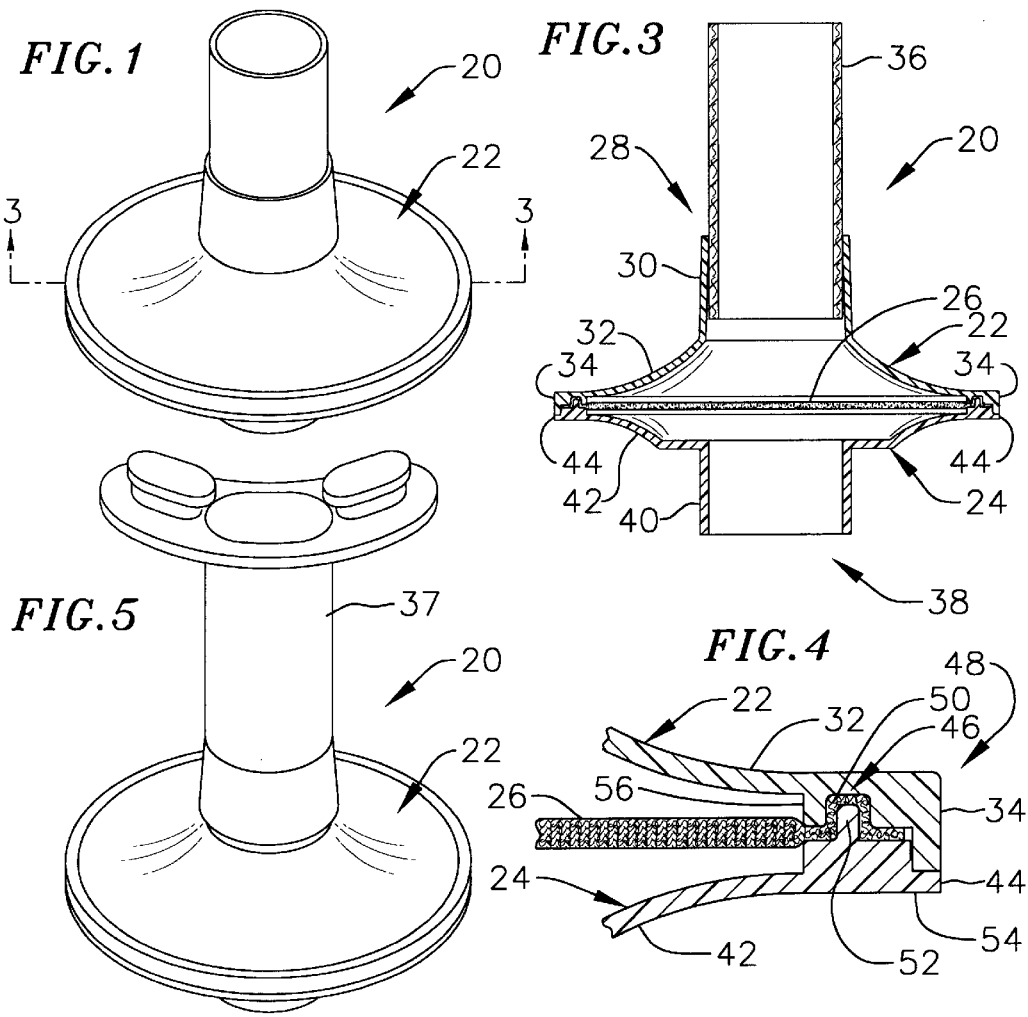
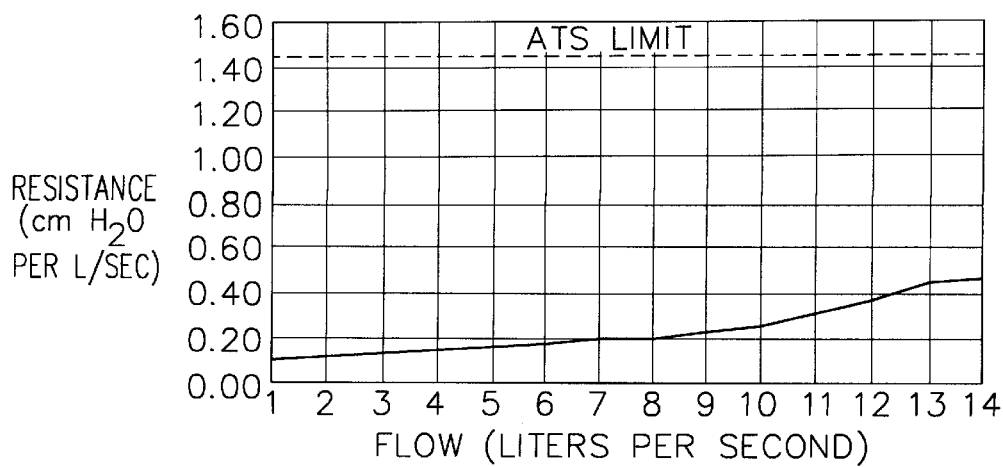

APPARATUS AND METHOD OF MANUFACTURING PULMONARY FUNCTION FILTER

I. BACKGROUND OF THE INVENTION

A. Field of the Invention

This invention relates to pulmonary function filters.

B. Related Art

Pulmonary function filters, traditionally used on medical devices such as spirometers and other respiratory function analyzers and treatment equipment, are intended primarily to remove viral and bacterial organisms from an air or other gas stream. They also remove particulates and any other matter such as moisture droplets contained in the gas stream. The size and effectiveness of the filter in removing these elements from the gas stream depend on the characteristics of the filter element used in the filter.

In the case of spirometry, the filter removes bacterial and viral organisms as well as particulates found in the exhalation stream coming from the patient. The filter also removes any matter entrained in the inhalation stream coming from the spirometer during inhalation.

The effectiveness of the filter depends on the actual filter element housed in the filter which captures the organisms and particulates. Filter effectiveness in turn depends upon proper positioning of the filter element and ensuring that the configuration of the filter element remains unchanged during normal use. If the filter element collapses, gases can pass around the edges of the filter element, and, to that extent, are not filtered. If a filter element contacts the wall of the filter housing, little if any gas flow passes from one side of the filter to the other at the area of contact, thereby reducing the effective surface area of the filter element. Gas flow may thereby be reduced, increasing the back pressure inhibiting free flow of gas through the filter.

Fins or pins may be used on the surface of the filter housing to hold the filter element off the housing wall. Fins form eddy currents and vortices in the gases flowing through the filter, and somewhat reduce the free gas volume within the filter housing. They also form condensation points for moisture in the gases passing through the filter. Consequently, they reduce filter effectiveness. If the circumferential edges of the filter element are clamped between circumferential edges of two halves of the filter housing, the filter element might be held in place approximately centered in the filter housing in order to hold the filter element taut. However, the filter element can flex and loosen from between the two halves of the filter housing reducing the overall effectiveness of the filter.

SUMMARY OF THE INVENTION

An apparatus is described along with a method of manufacturing a pulmonary function filter which holds a filter element in place within a filter housing in a manner which minimizes the possibility of stretching or movement of the filter element within the housing. The filter permits flow-through the filter element within the filter housing unobstructive by any pins or fins which might otherwise be used to properly position the filter element. The filter minimizes the possibility of wrinkling of the filter element, thereby permitting improved flow and filtration characteristics.

In accordance with one aspect of the invention, a pulmonary function filter includes a housing and a filter element having a perimeter edge positioned or held in place by perimeter elements of the filter housing. In one preferred embodiment, the perimeter edge of the filter element is positioned relative to the upper and lower perimeter elements of the housing in such a way that the perimeter edge of the filter element approximately reverses itself relative to another portion of the perimeter edge. In another preferred embodiment, the filter element perimeter edge is held in place between upper and lower perimeter elements of the housing by following at least three turns within a path defined by the mating perimeter edges of the housing. Preferably, at least three turns are right angle turns to insure a suitable frictional fit between the housing and the filter element. In a further preferred embodiment, four right angle turns are made by the perimeter edge of the filter element.

In the configuration of the present invention, the filter element is placed under tension in the housing when the housing elements are mated together. Tensioning of the filter element can be most easily accomplished by forming a groove in one perimeter portion of the lower housing and forming a complimentary annulus or ring on the perimeter portion of the upper housing which presses a perimeter edge of the filter element into the groove. Preferably, the groove is formed by adjacent walls that are perpendicular relative to each other to form the U-shaped groove or channel.

Upon assembly, the perimeter edge of the filter element is pressed into the groove. Because of the substantially right-angle corners at the rim of the groove, and also partly because of the tight interference fit of the filter element into the groove with the annulus, slippage of the filter element is substantially prevented. Consequently, the entire filter element is somewhat stretched as the two housing elements join. The stretching of the filter element, as well as, the interlocking housing portions with the filter element fixes the filter element in place in a relatively taut condition.

Having the filter element under some tension helps to hold the filter element in place, and helps to minimize any obstruction to free-flow of air (or gases) through the filter. The active filtration area of the filter element does not contact the walls of the filter housing, and there are no pins or fins to position the filter element, and which may cause vortices and condensation points during normal operation. It is believed that air flow is improved in this configuration, and filtration characteristics are also improved. The design also minimizes flow resistance and permits reduction in dead air space and provides high filtration efficiency. Any vibration or movement of the filter element is minimized and the filter element is held in place only at locations on the filter element that are not active filtration areas.

As another aspect of the present invention, the upper and lower filter housing elements are joined and bonded through use of a sonic shear joint which minimizes external flashing or flow of material during the welding process. Such a shear joint improves interference fit during assembly.

In accordance with one aspect of the present invention, the upper and lower filter housing elements are joined by fitting an outer rim over an inner ring. The outer rim preferably has an internal circumferential wall which mates with an outwardly facing circumferential wall on the inner wall. The shear joint is formed by placing a bead near the portion of the outwardly facing wall which is closest adjacent the end of the rim on the mating section of the filter housing.

These and other aspects of the present inventions are shown in the accompanying drawings, a brief description of which follows, as well as upon consideration of the detailed description of the preferred embodiments.

A method is also described which is used to assemble the filter housing and the filter element in such a way that the filter element is placed and held under tension during normal operation. Two mating filter elements are used which have complimentary surfaces to interengage a perimeter edge of the filter element. The filter element is placed over one of the filter housing elements and the other filter housing element joined to the first. The perimeter edge of the filter element is pressed between the first and second filter housing elements to stretch the filter element material and to hold the filter element in place. The filter housing elements can then be bonded, sealed or otherwise fixed together to keep the filter element in place.

BRIEF DESCRIPTION OF THE DRAWINGS

FIG. 1 is a top isometric view of a pulmonary function filter, including a mouthpiece.

FIG. 3 is a side cross sectional view of the filter of FIG. 1 taken along lines 3—3.

FIG. 4 is a detailed side cross section showing the joining of the upper and lower filter housing elements with the filter element.

FIG. 5 is a top isometric view of the filter of FIG. 1 including a bite mouthpiece.

FIG. 6 is a graphic illustration showing flow resistance as a function of flow.

DETAILED DESCRIPTION OF THE PREFERRED EMBODIMENTS

Figure 2:
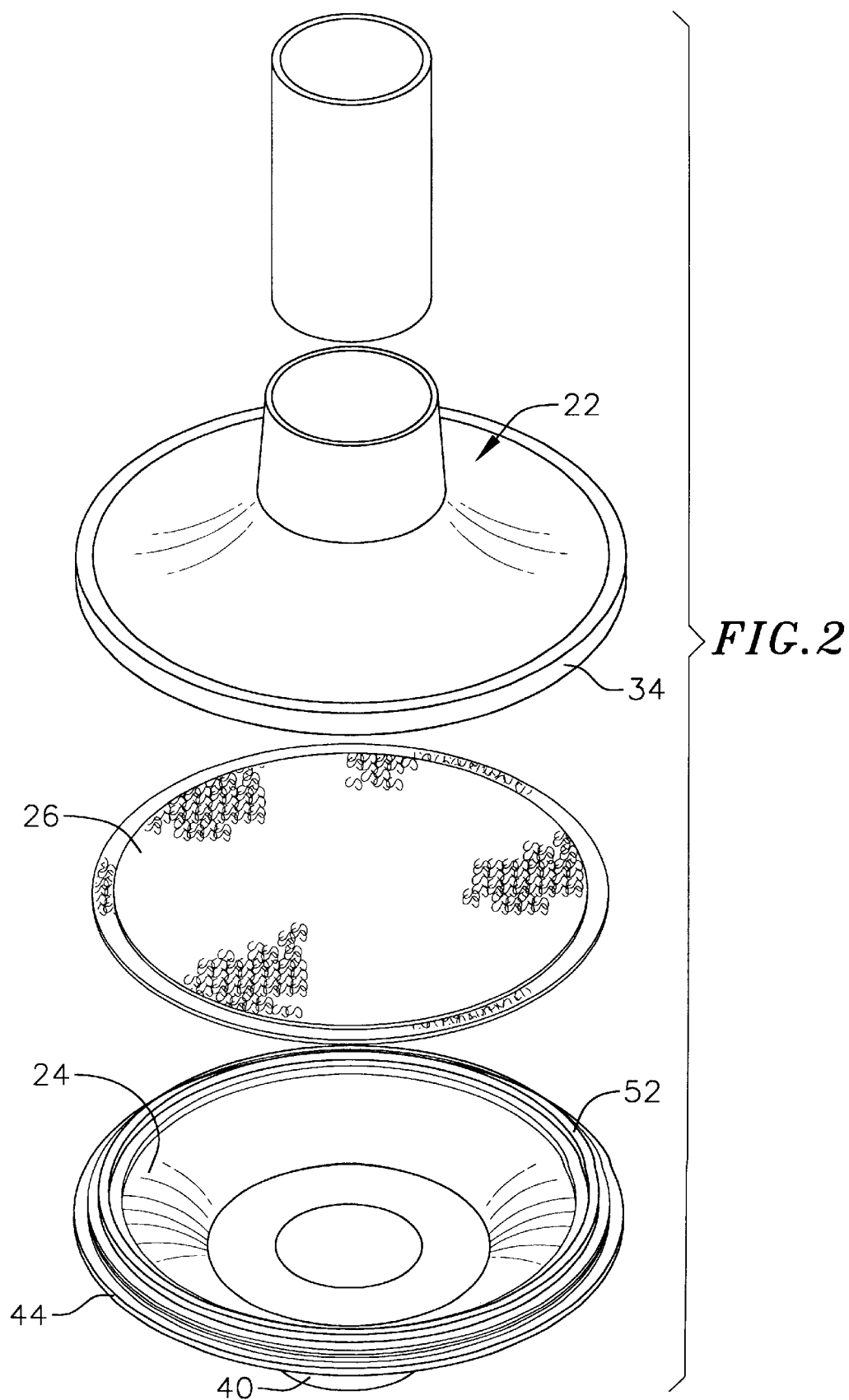
FIG. 2 is a top perspective and exploded view of the pulmonary function filter of FIG. 1 showing the elements of the filter with the mouthpiece.

A pulmonary function filter is described which includes a filter element held in place under slight tension and which enhances air flow through the filter. The described filter also minimizes any filter element movement during normal operation and eliminates obstructions to air flow which would exist with fins or pins to position the filter element. Flow resistance is minimized and dead air space is minimized as well.

A pulmonary function filter 20 (FIGS. 1–5) includes an upper filter housing element 22 and a lower filter housing element 24. The filter also includes a filter element 26 (FIGS. 2–4) held in place preferably through interengagement between the upper and lower housing elements. The upper housing element 22 includes an outlet 28 formed by an upper cylindrical wall 30. The upper wall 30 is preferably integral with the upstream housing wall 32 extending from the upper wall 30 to the outer perimeter edge 34 of the upper housing element. A mouthpiece 36 can be inserted into the inlet 28 within the upper cylindrical wall 30.

The lower housing element 24 includes an outlet 38 defined by a lower cylindrical wall 40 for connection to an appropriate instrument. The instrument may have any number of functions such as spirometry, and the like. The lower cylindrical wall 40 is coupled to a downstream housing wall 42 which extends to an outer perimeter wall 44 to join with the outer perimeter wall 34 of the upper housing element.

The mouthpiece 36 can be removed and replaced by a bite adapter 37 fitting over the outside of the cylindrical wall 30. (See FIG. 5).

The upper housing element 22 includes a groove 46 facing a lower housing element 24 and extending around the perimeter or circumference of the upper housing element. As shown in FIGS. 1, 2 and 5, the upper and lower housing elements are preferably substantially circular. The groove 46 is formed in the outer perimeter edge 48 of the upper housing element 22. The groove 46 is sufficiently wide and deep to accept a part 50 of the outer perimeter edge portion of the filter element along with an annular wall 52 extending upwardly from an outer perimeter edge 54 of the lower housing 24. The width and depth of the groove 46 and the width of the annular wall 52 are sized to sufficiently engage and push the outer perimeter of the filter element 50 into the groove 46 and hold it in place during normal operation, as well as to slightly stretch the filter element as it is being sandwiched between the upper and lower housing elements.

The groove 46 is preferably a square U-shaped groove and is defined on its interior side by a wall 56 having a first relatively right-angled corner 58, a flat end 60 and a second relatively right-angled corner 62 for engaging the material of the filter element. The inside of the groove is defined by a first interior groove wall 64, a bottom wall 66 and a second interior wall 68. The walls 64, 66 and 68 preferably join at approximate right angles and are sized so as to assist in holding the part of the filter element pressed into the groove 46 by the annular wall 52. The groove, annular wall 52 and the wall 56 are all preferably circular to ensure adequate mating of the parts upon assembly.

The outer perimeter edge 48 of the upper housing extends on the interior side from the second interior wall 68 radially outwardly to a mating wall 70, extending from the outer perimeter edge 48 toward the lower housing element 24 in order to provide an adequate fit and joinder of the upper and lower housing elements. The mating wall 70 preferably joins the outer perimeter edge 48 at a substantially right angle 72 and forms, on the outside of the outer perimeter edge, part of the outer perimeter surface 34 of the upper housing. Part of the inside surface of the mating wall 70 also provides a sealing or welding surface for sonically welding the upper and lower housing elements.

The lower housing element 24 extends outwardly to the outer perimeter edge 54, terminating at the outer perimeter surface 44. The outer perimeter edge 54 includes a base 74 extending inwardly toward the upper housing element. The base is preferably circular and includes an interior wall 76 complimentary to the interior wall 56 on the upper housing element. The base includes a first substantially right angle corner 78 to form a first base wall 80 extending from the right angle corner 78 to the base of the annular wall 52. The annular wall 52 joins at the base at a second right angle corner 82 on the interior side and a third right angle corner 84 on the exterior side. The annular wall 52 includes an interior surface 86 and an exterior surface 88 defining an end wall 90 having a third substantially right angle corner 92 and a fourth substantially right angle corner 94.

The third right angle corner 84 forms a termination point for the second base wall 96 extending radially outwardly to a base perimeter wall 98. The base perimeter wall 98 engages the mating wall 70 to join the upper and lower housing elements.

The base perimeter wall 98 further includes a shear joint 100 for ultrasonically welding the upper and lower housing elements together. The shear joint extends circumferentially around the base perimeter wall 98 and extends from the corner defined by the base perimeter wall 98 and the outer perimeter edge 44 upwardly approximately half the height of the base perimeter wall 98. The shear joint 100 provides a reliable interference fit upon joinder of the upper and lower housing elements, and is located interior to the outer perimeter edges 34 and 44 of the housing elements to reduce the likelihood of visible material flow at the edges of the housing elements, or flashing.

Figure 7:
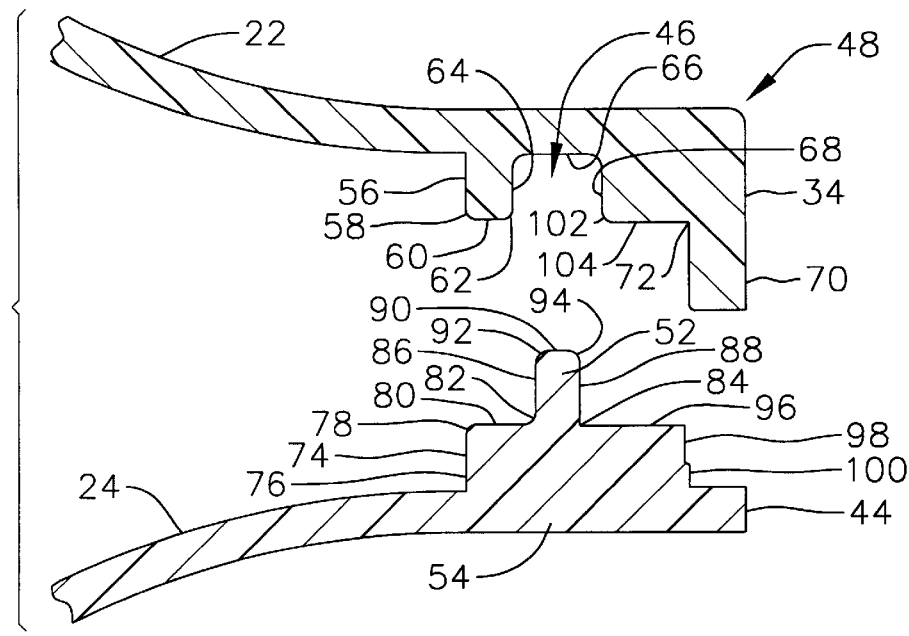
FIG. 7 is an enlarged view of the perimeter edge portions of the upper and lower housing elements in accordance with an aspect of the present invention.
Figure 8:
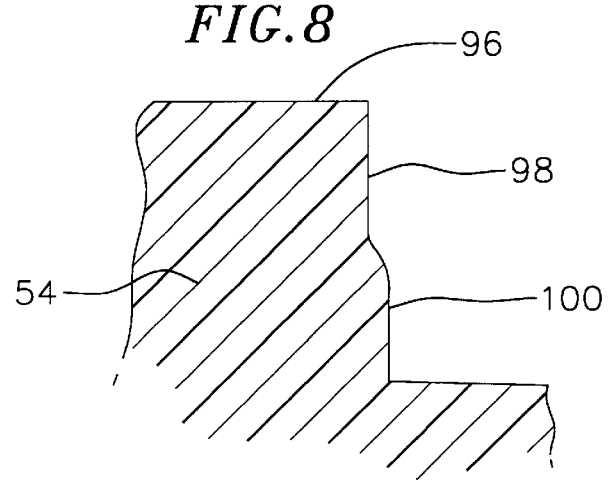
FIG. 8 is a detailed cross sectional view of the outer perimeter portion of the lower housing element showing a sheer joint.

The described right angles are preferably as close to a 90° angle as permitted within the design and tolerance requirements for plastics, molding or other material handling requirements. It is believed that the right angles optimize not only the interfitting of the upper and lower housing elements, but also optimize the holding of the perimeter edge portion of the filter element. For example, as the perimeter edge portion of the filter element is pressed into the groove 46 by the annular wall 52, the third right angle 102 (FIG. 7) helps to hold the filter element material in place as the material is pressed into the groove. At the same time, the second right angle 62 also helps to hold the material in place and provides some symmetry or balance between the holding at the angle 102 and at the angle 62. While it is possible that some slippage may occur in the filter element along the surfaces which it is contacting, the net result is that some stretching occurs in the filter element as the perimeter edge portion of the filter element is pressed into the groove by the annular wall 52.

The perimeter edge portion of the filter element is held in place by the groove and the annular wall 52 through contact at each of the corners 62 and 102, as well as at the corners 92 and 94, and further in addition to the contact over the walls defining those corners along with the opposite walls in the opposite housing elements.

Figure 9:
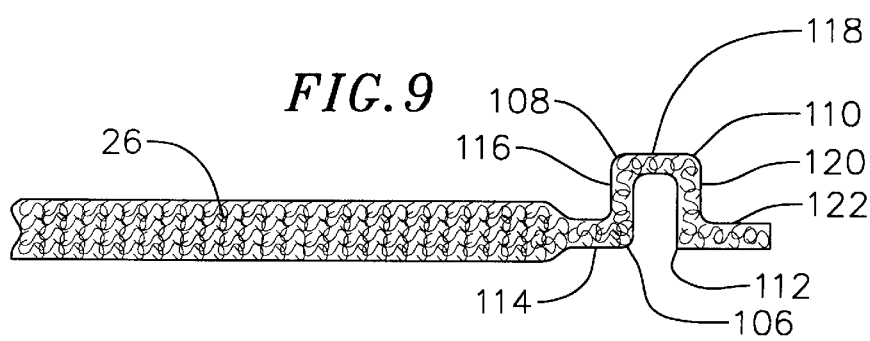
FIG. 9 is a detail sectional drawing showing the configuration of the perimeter edge portion of the filter element when positioned between the upper and lower housing elements.

It is believed that the holding and retention of the filter element perimeter portion is achieved through contact of the wall 56 and the base wall 80, the annular wall 52 and the walls of the groove 46 as well as the base wall 96 and the opposing wall 104. Retention of the filter element is achieved through a combination of pressure and frictional engagement created by the first, second, third and fourth right angle turns formed in the filter element through the joinder of the upper and lower housing elements. As shown in FIG. 9, the filter element 26 is pressed into a configuration which includes a first right angle corner 106, a second right angle corner 108, a third right angle corner 110, and a fourth right angle corner 112. The perimeter edge portion of the filter element is pressed between the upper and lower housings to form a first leg 114, a second leg 116 extending between the first corner 106 and the second corner 108, a third leg 118 between the second and third corners 108 and 110, respectively, a fourth leg 120 between the third and fourth corners 110 and 112, respectively, and a fifth leg 122 extending from the fourth corner 112. The first and fifth legs 114 and 122, respectively, extend in the same plane as the filter element, and the third leg 118 is parallel to the first and fifth legs. The second and fourth legs are substantially parallel, but extend in substantially opposite directions. It is believed that the reversal of direction of the legs of the filter element enhance the holding ability of the final assembly, and that the right angles formed in the several elements also enhance the holding ability.

For assembly, the upper housing element 22 is inverted and the filter element 26 placed over the opening so that the outer perimeter edge portion of the filter element 26 covers the groove 46 and the walls 60 and 104. The lower housing element is then inverted and pressed into engagement with the outer perimeter portion of the filter element and the upper housing so that the annular wall 52 presses the perimeter edge portion of the filter element into the groove 46. The edge portion of the filter element is engaged by the various corners and walls to minimize any slippage of the filter element along the surfaces, and to increase the amount of stretching of the filter element to hold it in place and to produce a taut configuration.

The assembled pulmonary function filter is assembled so that the filter element has a perimeter edge portion positioned between the upper and lower perimeter housing elements and the filter perimeter edge portion follows a path extending at least partially back on itself, thereby enhancing the ability to hold the filter element in place. In a preferred embodiment, the perimeter edge portion of the filter follows several right angle turns, several of which are perpendicular to the plane of the filter element. Preferably, the filter elements perimeter edge portion follows at least three and preferably four turns to ensure holding of the perimeter filter edge portion in the housing and to hold the filter element taut. Preferably, the turns are right angle turns. The positioning and holding of the filter element eliminates any need for fins, guides or pins to hold the filter element away from the walls of the housing, and permits reduction of the amount of dead air space in the overall filter. By holding the filter element taut, there is relatively little movement in the filter element during normal use, and the pins and fins can be avoided. The filter still maintains a high filtration efficiency and low flow resistance.

The shear joint can be used to create a hermetic seal and provides for ultrasonic welding on two different surfaces of the joint while still reducing the likelihood of any flashing.

FIG. 6 shows a representative curve of flow resistance as a function of flow. The curve shows a relatively low flow resistance over a substantial flow rate, with a relatively gradual rise in resistance over a relatively substantial increase in flow.

It should be noted that the above are preferred configurations but others are foreseeable. The described embodiments of the invention are only considered to be preferred and illustrative of the inventive concept; the scope of the invention is not to be restricted to such embodiments. Various and numerous other arrangements may be devised by one skilled in the art withou departing from the spirit and scope of the invention.

What is claimed is:

1. A pulmonary function filter comprising a housing having an inlet and an outlet and a perimeter edge formed by an upper perimeter element and a lower perimeter element and a filter element having a planar portion and a perimeter edge portion positioned between the upper and lower perimeter elements, and wherein the filter element perimeter edge portion includes a first perimeter portion which extends substantially perpendicular to the planar portion, a second perimeter portion which extends substantially perpendicular to the first portion and a third perimeter portion perpendicular to the second and substantially parallel to the first.

2. The filter of claim 1 wherein the housing includes a first housing and a second housing and wherein the second housing includes a housing groove facing toward the filter element perimeter edge portion and defined by a first side, bottom and second side walls and wherein the first housing includes a first housing wall facing toward the filter element perimeter edge portion and complementary to the groove.

3. The filter of claim 1 wherein the filter element is placed in the housing under tension.

4. A pulmonary function filter comprising a housing having an inlet and an outlet and a perimeter edge formed by an upper perimeter element and a lower perimeter element and a filter element having a perimeter edge held between the upper and lower perimeter elements and wherein the filter element perimeter edge follows at least three right angle turns.

5. The filter of claim 4 further comprising a fourth turn.

6. The filter of claim 5 wherein the turns are right angle turns.

7. The filter of claim 6 wherein the filter element perimeter edge extends in at least two different directions which are at least partially opposite directions.

8. The filter of claim 4 wherein the filter element is substantially planar and includes an intermediate filter element between the planar portion and the perimeter edge portion and wherein the intermediate filter element extends from the plane of the planar filter element portion.

9. The filter of claim 4 wherein the filter element is placed in the housing under tension.

10. A pulmonary function filter comprising a housing having an inlet and an outlet and a perimeter edge formed by an upper perimeter element and a lower perimeter element, the upper perimeter element including a projection extending toward the lower perimeter element when the upper and lower perimeter elements are assembled, the lower perimeter element including a recess for accommodating the projection of the upper housing element, and a filter element having a perimeter edge portion positioned between the upper and lower perimeter elements and wherein the filter element perimeter edge is positioned between the projection of the upper perimeter element and the recess of the lower perimeter element and wherein the filter element perimeter edge portion follows a U-shaped path to reach the perimeter edge of the filter element.

* * * * *